United States Patent
Cahill

(10) Patent No.: US 8,715,319 B2
(45) Date of Patent: May 6, 2014

(54) CATCH MEMBER FOR SEPTAL OCCLUDER WITH ADJUSTABLE-LENGTH CENTER JOINT

(75) Inventor: Ryan Cahill, Newtonville, MA (US)

(73) Assignee: W.L. Gore & Associates, Inc., Flagstaff, AZ (US)

( * ) Notice: Subject to any disclaimer, the term of this patent is extended or adjusted under 35 U.S.C. 154(b) by 1107 days.

(21) Appl. No.: 12/237,723

(22) Filed: Sep. 25, 2008

(65) Prior Publication Data

US 2009/0088795 A1    Apr. 2, 2009

Related U.S. Application Data

(60) Provisional application No. 60/976,041, filed on Sep. 28, 2007.

(51) Int. Cl.
  *A61B 17/08*    (2006.01)
(52) U.S. Cl.
  USPC .............................. 606/215; 606/213; 606/157
(58) Field of Classification Search
  USPC .......................... 606/151, 157, 213, 215, 216
  See application file for complete search history.

(56) References Cited

U.S. PATENT DOCUMENTS

| | | | | |
|---|---|---|---|---|
| 5,171,259 | A * | 12/1992 | Inoue | 606/213 |
| 5,702,421 | A * | 12/1997 | Schneidt | 606/213 |
| 6,548,569 | B1 | 4/2003 | Williams et al. | |
| 6,610,764 | B1 | 8/2003 | Martin et al. | |
| 6,685,707 | B2 * | 2/2004 | Roman et al. | 606/916 |
| 2003/0181945 | A1 | 9/2003 | Opolski et al. | |
| 2004/0044361 | A1 * | 3/2004 | Frazier et al. | 606/200 |
| 2004/0044364 | A1 * | 3/2004 | DeVries et al. | 606/213 |
| 2004/0220610 | A1 | 11/2004 | Kreidler et al. | |
| 2005/0043759 | A1 | 2/2005 | Chanduszko | |
| 2005/0053416 | A1 | 3/2005 | Kwan | |
| 2005/0234509 | A1 | 10/2005 | Widomski et al. | |
| 2005/0267523 | A1 | 12/2005 | Devellian et al. | |
| 2005/0273135 | A1 * | 12/2005 | Chanduszko et al. | 606/213 |
| 2006/0052821 | A1 | 3/2006 | Abbott et al. | |

(Continued)

FOREIGN PATENT DOCUMENTS

| | | |
|---|---|---|
| WO | WO 03/032818 | 4/2003 |
| WO | WO 2006/028813 | 3/2006 |

OTHER PUBLICATIONS

U.S. Appl. No. 11/728,694, Callaghan.
U.S. Appl. No. 60/1787,988, Callaghan.

(Continued)

*Primary Examiner* — Corrine M McDermott
*Assistant Examiner* — Alexander Orkin
(74) *Attorney, Agent, or Firm* — DLA Piper LLP (US)

(57) ABSTRACT

A collapsible medical device for occluding an aperture in a body, e.g., a patent foramen ovale (PFO), is disclosed. The device includes a distal end and a distal portion for contacting the distal side of tissue, a proximal end and a proximal portion for contacting the proximal side tissue, a center joint for extending through the aperture and being hollow in the center. The center joint engages the distal and proximal portions and has a variable length to accommodate tissues of different thickness. The device also includes a catch system for holding the collapsible medical device in an expanded configuration. The catch system includes a distal threaded catch portion engaging the distal end and a proximal threaded catch portion engaging the proximate end. The threaded portions rotate relative to one another and cooperate through the center joint to vary a distance between the distal and proximal ends.

18 Claims, 13 Drawing Sheets

(56) References Cited

U.S. PATENT DOCUMENTS

| | | |
|---|---|---|
| 2006/0122647 A1 | 6/2006 | Callaghan et al. |
| 2006/0241687 A1 | 10/2006 | Glaser et al. |
| 2006/0265004 A1 | 11/2006 | Callaghan et al. |
| 2007/0010851 A1 | 1/2007 | Chanduszko et al. |
| 2007/0073337 A1 | 3/2007 | Abbott et al. |
| 2007/0129755 A1 | 6/2007 | Abbott et al. |
| 2007/0167981 A1 | 7/2007 | Opolski |
| 2007/0250081 A1* | 10/2007 | Cahill et al. .................. 606/151 |
| 2007/0282430 A1* | 12/2007 | Thommen et al. ........... 623/1.22 |

OTHER PUBLICATIONS

U.S. Appl. No. 60/847,703, Cahill.

* cited by examiner

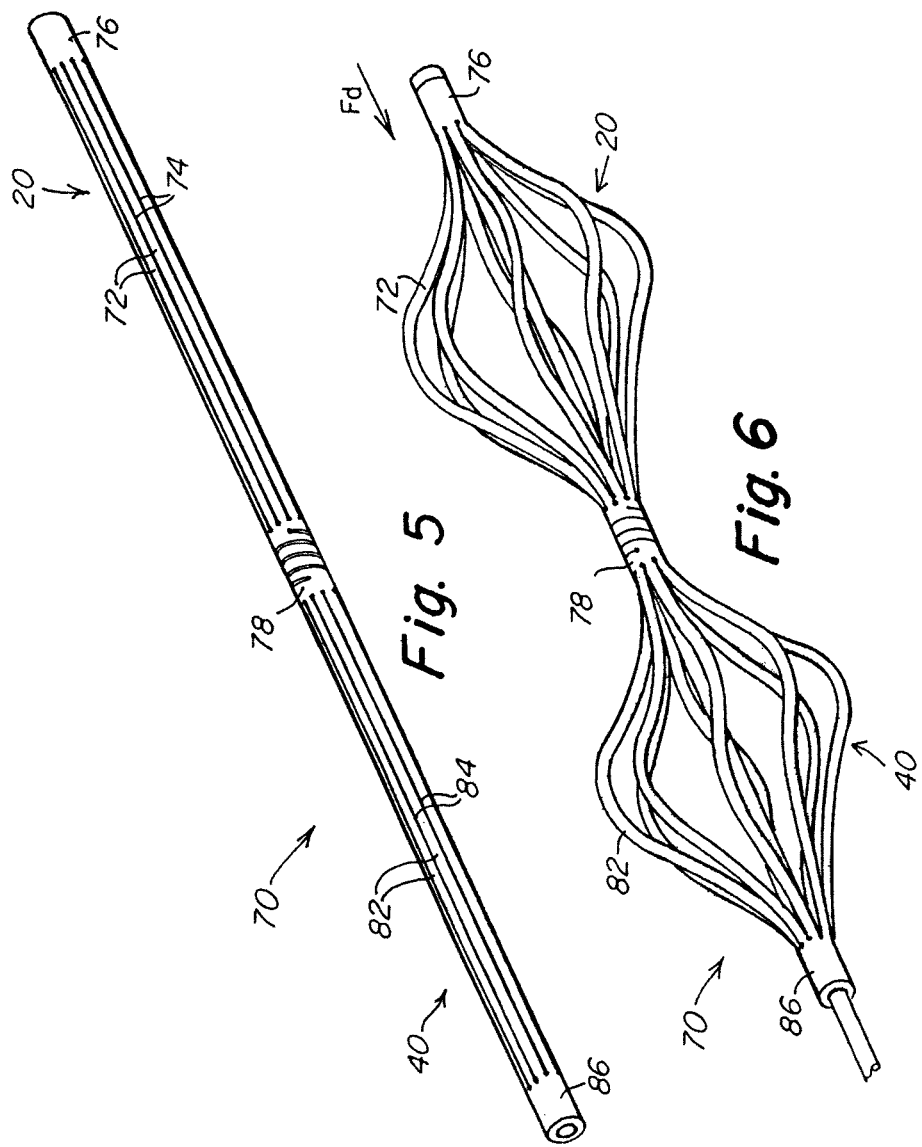

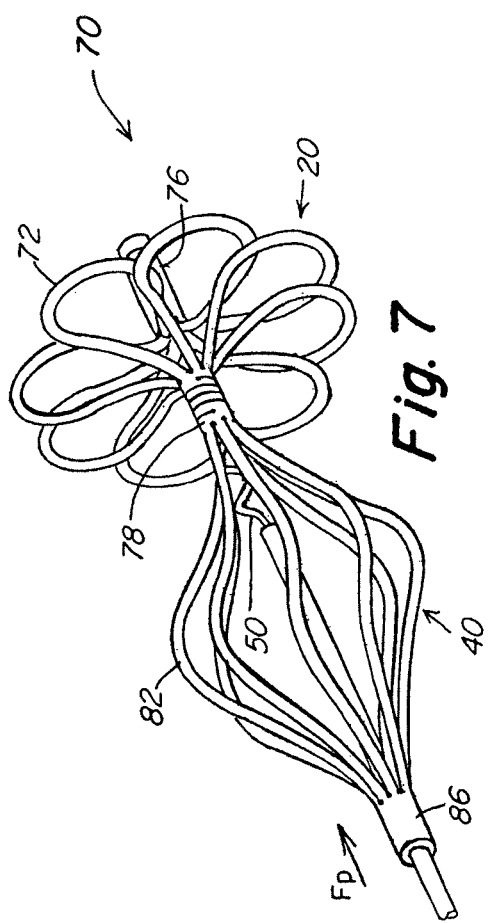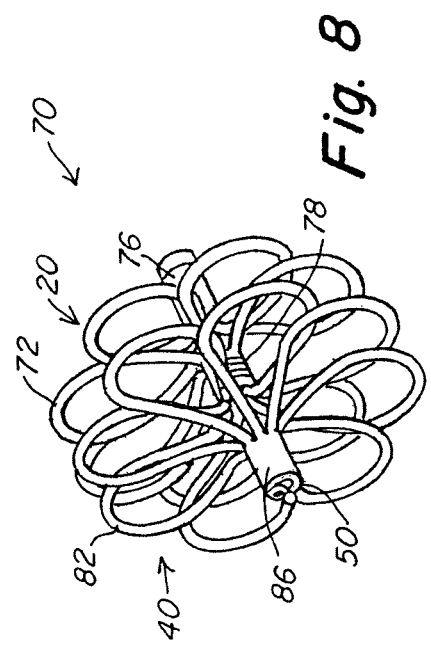

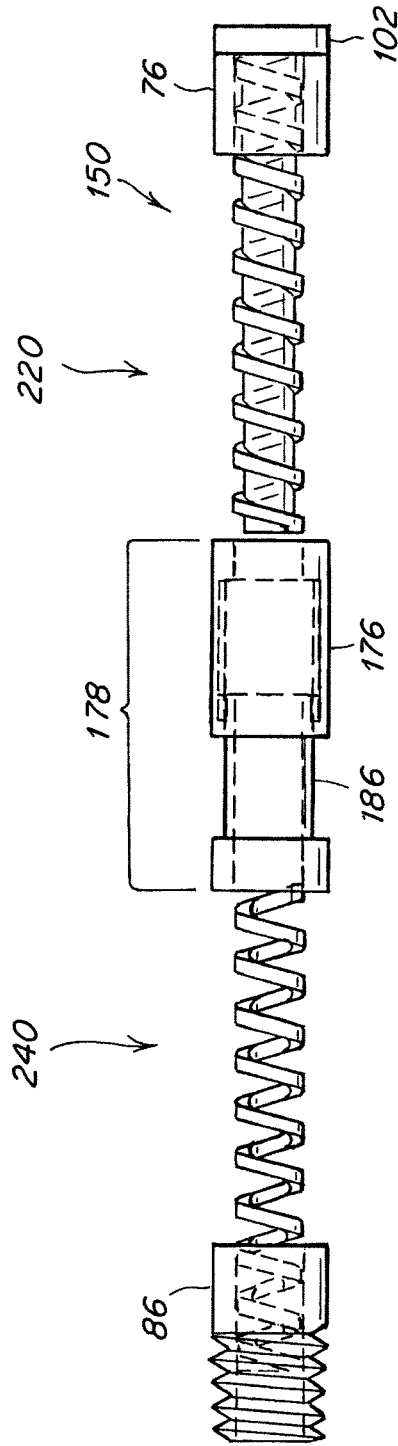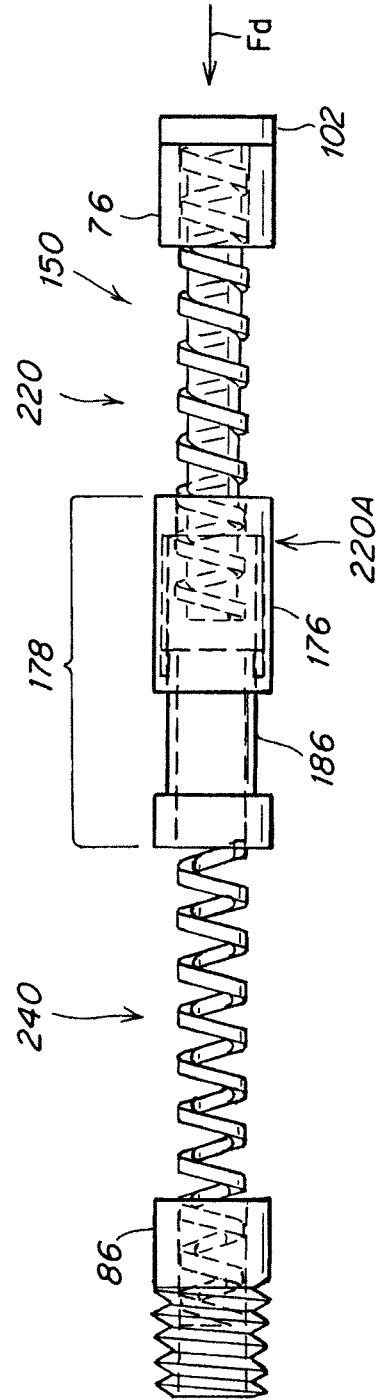

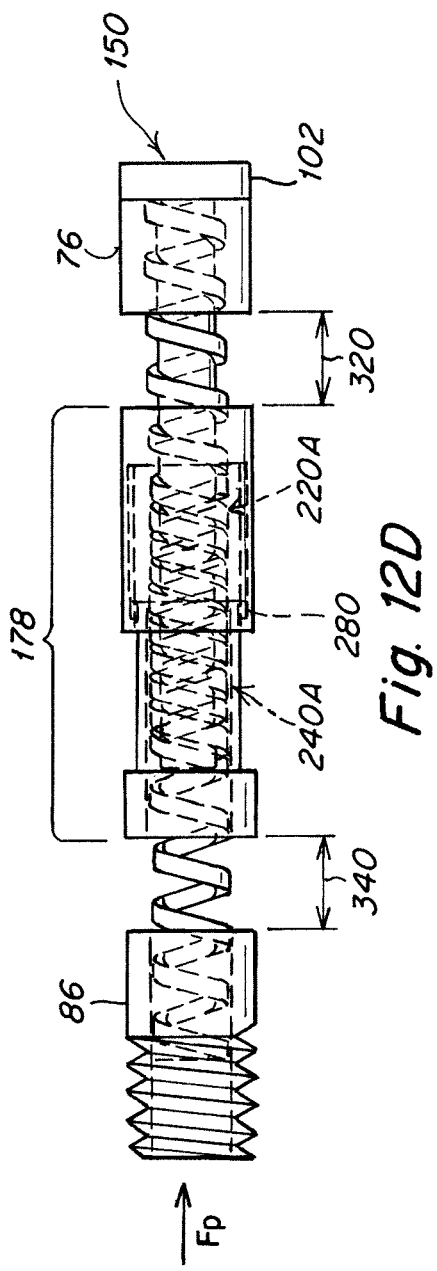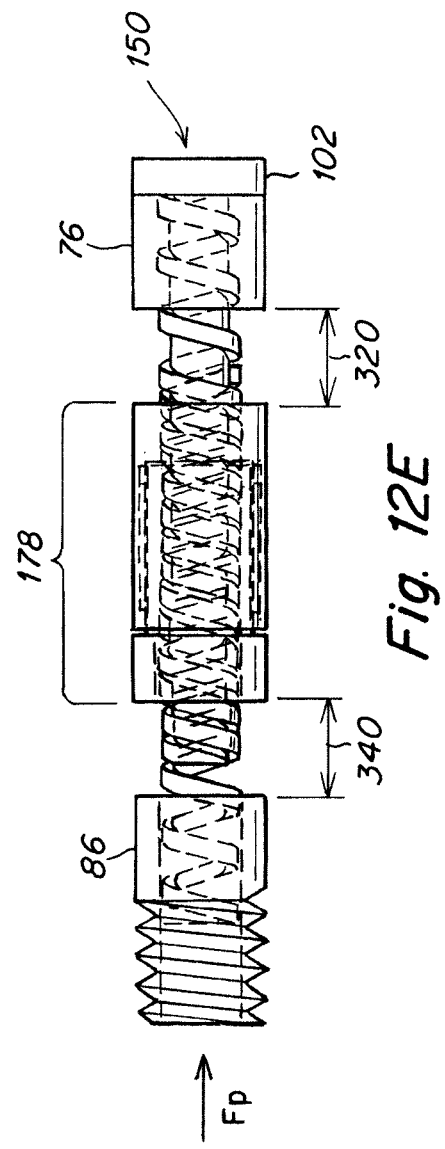

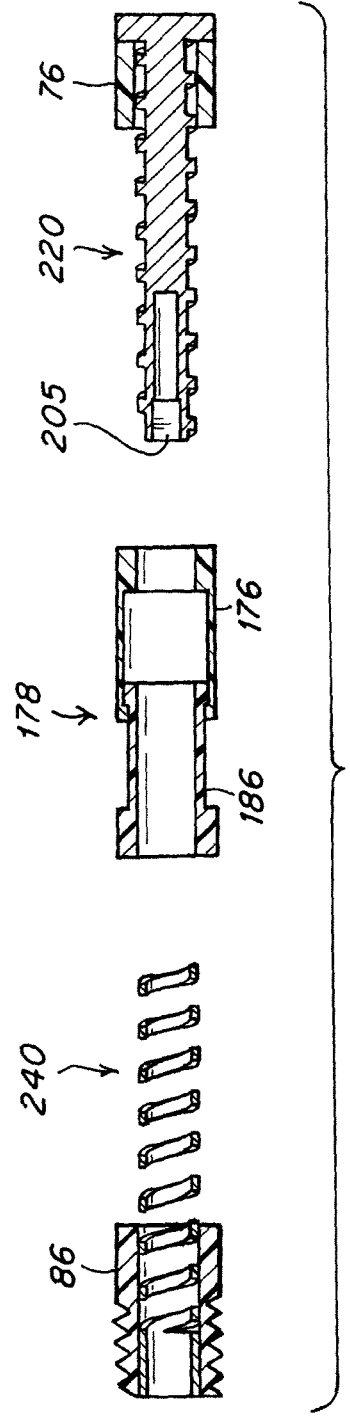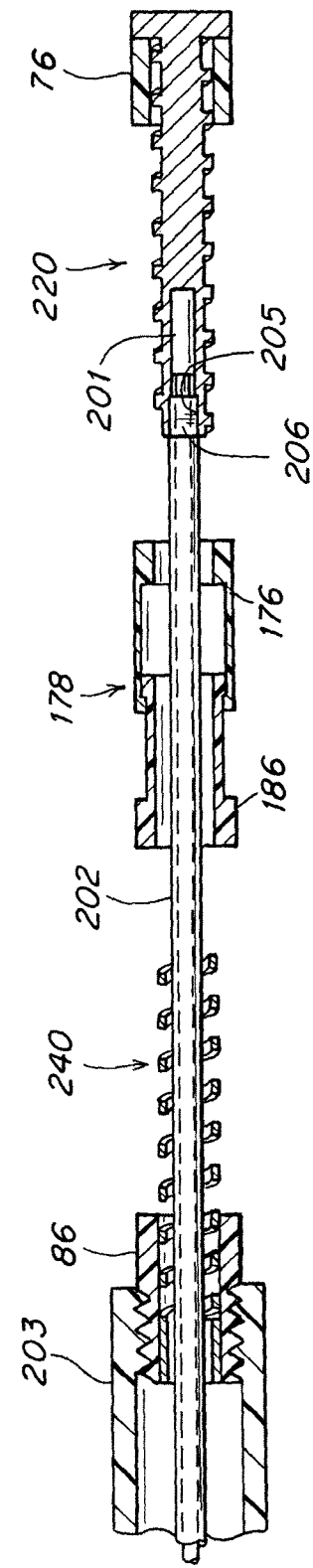

CATCH MEMBER FOR SEPTAL OCCLUDER WITH ADJUSTABLE-LENGTH CENTER JOINT

CROSS-REFERENCE TO RELATED APPLICATIONS

This application claims the benefit under 35 U.S.C. §119 (e) to U.S. Provisional Patent Application No. 60/976,041, entitled Catch Member For Septal Occluder With Adjustable-Length Center Joint, filed Sep. 28, 2007, the contents of which are incorporated by reference herein.

The present invention is related to U.S. patent application Ser. No. 11/729,636 filed Mar. 29, 2007, entitled Adjustable Length Patent Foramen Ovale (PFO) Occluder and Catch System, the entire contents of which is herein incorporated by reference.

FIELD OF THE INVENTION

This invention relates generally to occlusion devices for the closure of physical anomalies, such as an atrial septal defect, a patent foramen ovale, and other septal and vascular defects, and more particularly to catch members for septal occluders with adjustable-length center joints.

BACKGROUND OF THE INVENTION

A patent foramen ovale (PFO), illustrated in FIG. 1, is a persistent, one-way, usually flap-like opening in the wall between the right atrium 11 and left atrium 13 of the heart 10. Because left atrial (LA) pressure is normally higher than right atrial (RA) pressure, the flap usually stays closed. Under certain conditions, however, right atrial pressure can exceed left atrial pressure, creating the possibility that blood could pass from the right atrium 11 to the left atrium 13 and blood clots could enter the systemic circulation. It is desirable that this circumstance be eliminated.

The foramen ovale serves a definite purpose when a fetus is gestating. Because blood is oxygenated through the umbilical cord, and not through the developing lungs, the circulatory system of the fetal heart allows the blood to flow through the foramen ovale as a physiologic conduit for right-to-left shunting. After birth, with the establishment of pulmonary circulation, the increased left atrial blood flow and pressure results in functional closure of the foramen ovale. This functional closure is subsequently followed by anatomical closure of the two overlapping layers of tissue: septum primum 14 and septum secundum 16. However, a PFO has been shown to persist in a number of adults.

The presence of a PFO is generally considered to have no therapeutic consequence in otherwise healthy adults. Paradoxical embolism via a PFO is considered in the diagnosis for patients who have suffered a stroke or transient ischemic attack (TIA) in the presence of a PFO and without another identified cause. While there is currently no definitive proof of a cause-effect relationship, many studies have confirmed a strong association between the presence of a PFO and the risk for paradoxical embolism or stroke. In addition, there is significant evidence that patients with a PFO who have had a cerebral vascular event are at increased risk for future, recurrent cerebrovascular events. The presence of a PFO has also been linked to chronic migraine heachaches. Although researchers are still investigating the nature of the link, PFO closure has been shown to eliminate or significantly reduce migraine headaches in many patients.

Patients at such increased risks for therapeutic consequences are considered for prophylactic medical therapy to reduce the risk of a recurrent embolic event or other negative health effects. These patients are commonly treated with oral anticoagulants, which potentially have adverse side effects, such as hemorrhaging, hematoma, and interactions with a variety of other drugs. The use of these drugs can alter a person's recovery and necessitate adjustments in a person's daily living pattern.

In certain cases, such as when anticoagulation is contraindicated, surgery may be necessary or desirable to close a PFO. The surgery would typically include suturing a PFO closed by attaching septum secundum to septum primum. This sutured attachment can be accomplished using either an interrupted or a continuous stitch and is a common way a surgeon shuts a PFO under direct visualization.

Umbrella devices and a variety of other similar mechanical closure devices, developed initially for percutaneous closure of atrial septal defects (ASDs), have been used in some instances to close PFOs. These devices potentially allow patients to avoid the side effects often associated with anticoagulation therapies and the risks of invasive surgery. However, umbrella devices and the like that are designed for ASDs are not optimally suited for use as PFO closure devices.

Currently available septal closure devices present drawbacks, including technically complex implantation procedures. Additionally, there are significant complications due to thrombus formation, fractures of the components, conduction system disturbances, perforations of heart tissue, and residual leaks. Many devices have a high septal profile and include large masses of foreign material, which may lead to unfavorable body adaptation of a device. Given that ASD devices are designed to occlude holes, many lack anatomic conformability to the flap-like anatomy of PFOs. Thus, when employing an ASD device to close a PFO, the narrow opening and the thin flap of the PFO may form impediments to proper deployment of the device. Even if an occlusive seal is formed, the device may be deployed in the heart on an angle, leaving some components insecurely seated against the septum and, thereby, risking thrombus formation due to hemodynamic disturbances. Finally, some septal closure devices are complex to manufacture, which may result in inconsistent product performance.

Various devices and delivery systems have been developed to deliver occluders and other medical devices through body lumens. Some known delivery systems are used to deliver devices that readily expand to a deployed configuration when removed from the delivery system. Other devices do not readily expand into a deployed configuration, and techniques are used to change the configuration of the device into the deployed configuration. In either case, once a device is delivered to the desired delivery site and deployed, the device must have a catch system that keeps the device in the deployed configuration.

The devices and techniques disclosed herein are designed to address these and other deficiencies of prior art septal closure devices and techniques for constructing these devices.

SUMMARY OF THE INVENTION

In a preferred embodiment, a collapsible medical device for occluding an aperture in a body includes a distal side and a proximal side. The medical device includes a first configuration with a reduced profile and a second configuration with an expanded profile and is adapted to be delivered through a delivery system into a desired delivery location. The medical device includes a distal end and a distal portion for contacting the distal side of the septal defect, a proximal end and a proximal portion for contacting the proximal side of the septal defect, a center joint for extending through the septal defect at an opening and being hollow in the center, the center joint engaging the distal portion and the proximal portion, and the center portion having a length, wherein the length can vary to accommodate tissues of different thickness and a catch system for holding the collapsible medical device in the second configuration, the catch system including a distal threaded catch portion engaging the distal end and a proximal threaded catch portion engaging the proximate end, the threaded portions rotating relative to one another and cooperating through the hollow center joint to enable a distance between the distal and proximal ends to vary.

In other embodiments, the medical device has a center joint that is a telescoping center joint. Alternatively, the medical device can include a locking mechanism to prevent movement of the threaded portions relative to one another after a desired center joint length has been achieved. In an embodiment, the medical device includes a center joint where the length of the center joint is variable when the medical device is in the first configuration and when in the second configuration. The medical device may be designed such that an axial force required to expand the length of the center joint is substantially equal to the force exerted by the catch system to achieve the expanded profile.

The medical device may include a catch system that is made of polymeric material including at least one of bioabsorbable polymeric material and shape-memory polymeric material. The medical device may also include a securement system for attaching the catch system to a delivery wire and attaching the medical device to a delivery catheter. The medical device may be constructed from a substantially cylindrical portion of material with a proximal and a distal series of axial slits, each series of axial slits arranged circumferentially.

A further embodiment of the invention includes a method of occluding an aperture in a body with an occluding device. The device includes a proximal portion, a distal portion, an adjustable-length center joint disposed between the proximal portion and the distal portion, and a catch system for holding the device in a deployed configuration. The method includes disposing the distal portion of the device on a first side of the aperture and the proximal portion of the device on a second side of the aperture. The method also includes reducing a distance between a distal end of the center joint and a distal end of the distal portion of the device to at least partial deploy the distal portion of the device and to engage a threaded distal section of the catch system with a threaded proximal section of the catch system. The method further includes rotating the threaded distal section of the catch system relative to the threaded proximal section of the catch system to increase the threaded engagement between the threaded proximal and distal sections of the catch system and to reduce a distance between a proximal end of the center joint and a proximal end of the proximal portion of the device to at least partial deploy the proximal portion of the device.

These and other embodiments will be further described with reference to the drawings below.

BRIEF DESCRIPTION OF THE DRAWINGS

In the Drawings:

FIGS. 5-8 illustrate an occluder according to an embodiment the present invention in a sequence between a reduced profile delivery configuration (FIG. 5) and an expanded profile deployed configuration (FIG. 8);

FIGS. 12A-E illustrate a catch member with an adjustable center joint for use with an adjustable-length occluder device, such as that shown in FIG. 11, according to an embodiment of the present invention;

FIGS. 13A-C illustrate a cross-sectional view of the catch member of FIG. 12 in conjunction with a rotational transfer shaft, according to an embodiment of the present invention;

DETAILED DESCRIPTION

The present disclosure provides devices intended to occlude an aperture within body tissue (occluders). In particular and as described in detail below, the described occluders may be used for closing an ASD, VSD or PFO in the heart. Although the embodiments are described with reference to an ASD, VSD or PFO, one skilled in the art will recognize that the devices and methods of the present invention may be used to treat other anatomical conditions. As such, the invention should not be considered limited in applicability to any particular anatomical condition. In addition, the systems and methods for delivery and retrieval, and for catching a device in a deployed state, which are aspects of the present invention, may also be used in connection with other types of devices besides an occluder, in particular, devices having tubular profiles.

Figure 1:
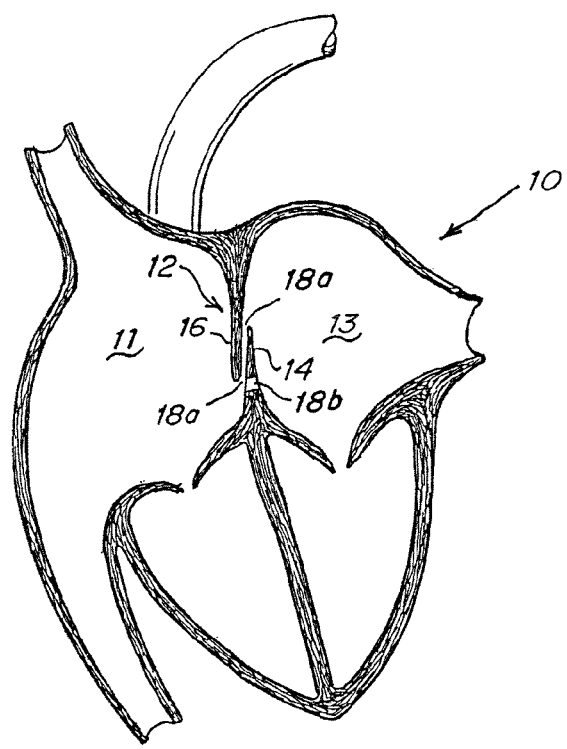
FIG. 1 is a schematic representation of a human heart including various septal defects.

FIG. 1 illustrates a human heart 10, having a right atrium 11 and a left atrium 13 and including various anatomical apertures 18a and 18b. The atrial septum 12 includes septum primum 14 and septum secundum 16. The anatomy of the septum 12 varies widely within the population. In some people, septum primum 14 extends to and overlaps with septum secundum 16. The septum primum 14 may be quite thin. When the anatomical aperture 18a is present, blood could travel through the anatomical aperture 18a between septum primum 14 and septum secundum 16 (referred to as "the PFO tunnel"). Additionally or alternatively, the presence of an ASD 18b could permit blood to travel through an aperture in the septum.

In this application, "distal" refers to the direction away from a reference location and "proximal" refers to the direction nearer the reference location (e.g., a catheter insertion location.). Additionally, the term "delivery configuration" refers to the configuration of a device, such as an occluder, when it has a reduced profile in a delivery catheter. The term "deployed configuration" refers to the configuration of the device, such as an occluder, when it has deployed from the catheter, such as at the desired implantation location. The reference numerals used to identify components of a described embodiment are disposed on multiple figures where the component is illustrated. The reference numerals are intended to facilitate an overall understanding of the invention and the relationship between components illustrated in different figures.

Figure 2:
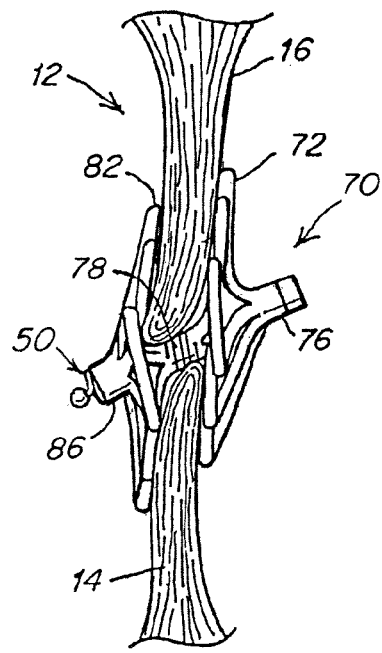
FIG. 2 illustrates a deployed occluder according to an embodiment of the present invention.

FIG. 2 illustrates an embodiment of an occluder 70 with which systems and techniques disclosed herein may be used. The occluder 70 is illustrated as deployed in the septum 12 of a heart, specifically, a PFO tunnel. The device operates to close the aperture in the septum by securing the septum primum 14 and septum secundum 16 in a closed manner.

As shown in FIGS. 5-8, the occluder 70 is formed from a tube (which can be extruded or rolled) that forms distal petals 72 produced by slits 74 in the distal portion 20 of the tube according to the cutting pattern shown in FIG. 5. As shown in FIG. 6, the distal portion 20 of the tube includes eight slits 74 that form the loops or petals 72. As apparent from the figures, the slits 74 are radially equally spaced along the circumference of the distal portion 20 of the tube so that loops of the same cross-sectional area are formed when deployed. Upon application of force $F_d$ to distal end 76, extended segments of the tube defined by slits 74 bow and twist outward to form distal petals 72 in distal portion 20 of the occluder 70. The movement of the distal petals 72 during deployment is such that the petals rotate in an orthogonal plane relative to the axis of the device.

Central joint 78 may be constrained (e.g., held within the confines of the catheter) during the application of force $F_d$. Any combination of forces sufficient to reduce the axial length of the tube may be applied, for example a combination of pulling and pushing may be used. One end of each of distal petals 72 originates from central joint 78, while the other end originates from distal end 76.

In a manner similar to the distal petals 72, proximal petals 82 are formed in proximal portion 40, as shown in FIGS. 5-8, by making slits 84 between central joint 78 and proximal end 86, using the same cutting pattern described above. Force $F_p$ can be used to create the proximal petals 82.

The tube(s) forming occluder 70 may be formed from a biocompatible material, for example, an alloy or polymer. In at least some embodiments, the occluder 70 is formed of a bioabsorbable material and/or a shape memory material. The thermal shape memory and/or superelastic properties of shape memory polymers and alloys permit the occluder 70 to resume and maintain its intended shape in vivo despite being distorted during the delivery process. Shape memory polymers can be advantageous because the structure of the device can assist in pressing the defect closed (e.g., the PFO tunnel). An illustrative biocompatible, shape memory alloy is nitinol. Alternatively, or additionally, the occluder 70 may be formed of a bioabsorbable metal, such as iron, magnesium, or combinations of these and similar materials. Exemplary bioabsorbable polymers include polyhydroxyalkanoate compositions, for example poly-4-hydroxybutyrate (P4HB) compositions, disclosed in U.S. Pat. No. 6,610,764, entitled Polyhydroxyalkanoate Compositions Having Controlled Degradation Rate and U.S. Pat. No. 6,548,569, entitled Medical Devices and Applications of Polyhydroxyalkanoate Polymers, both of which are incorporated by reference in their entirety.

The tube can be injection molded, extruded, or constructed of a sheet of material and rolled into a tube. The sheet of material could be a single ply sheet or multiple ply. The slits that form the petals (also called loops or struts) could be cut or stamped into the sheet prior to rolling the sheet into a tube to connect the ends to form an enclosed cross section. The tube can have various geometrical cross-sectional shapes, including circular or polygonal, e.g., square, hexagonal and octagonal, and the slits can be at the vertex or along the flat of a wall if the cross-section is of a particular geometry. Various attachment techniques can be used to join the ends of the sheet to form a tube, including welding, heat adhesives, non-heat adhesives and other joining techniques suitable for in-vivo application.

FIG. 8 illustrates the occluder 70 in a deployed configuration. The occluder 70 can be secured in the deployed configuration by a catch member that holds the ends of the tube together, certain embodiments of which are described below.

The embodiment described in conjunction with FIGS. 5-8 has some similarities to the device disclosed in U.S. patent application Ser. No. 10/890,784, entitled Tubular Patent Foramen Ovale (PFO) Closure Device with Locking Mechanism, filed on Jul. 14, 2004; U.S. patent application Ser. No. 11/111,685, entitled Closure Device with Hinges, filed on Apr. 21, 2005; U.S. patent application Ser. No. 11/395,718, entitled Tubular Patent Foramen Ovale (PFO) Closure Device with Catch System, filed Mar. 31, 2006; U.S. patent application Ser. No. 11/729,636, entitled Adjustable Length Patent Foramen Ovale (PFO) Occluder and Catch System, filed Mar. 29, 2007; U.S. patent application Ser. No. 11/728,694, entitled Patent Foramen Ovale (PFO) Closure Device with Linearly Elongating Petals, filed Mar. 27, 2007; all of which have the same assignee as the present application, and are incorporated by reference in their entirety. These incorporated documents describe how a device can be formed by making cuts or slits in a tube and compressing the ends. Additionally, U.S. patent application Ser. No. 11/093,360, entitled Center Joints for PFO Occluder, filed on Mar. 30, 2005 is incorporated by reference in its entirety.

The transformable design of occluder 70 enables occluder 70 to be delivered in a low profile, tubular form and to be converted readily, i.e., by reducing the axial length, in place to the high-profile deployed configuration. Moreover, the conversion can readily be effected by forcing distal end 76 and proximal end 86 together. For example, distal portion 20 and proximal portion 40 of occluder 70 may be deployed in separate steps, or both distal portion 20 and proximal portion 40 of occluder 70 may be exposed (e.g., out of the delivery catheter) prior to engaging the catch member and deployed together as the catch member is engaged. Use of the terms distal and proximal portion 20 and 40, respectively, include the petals or other geometries and configurations that are formed on the distal and proximal portions, respectively.

Occluder 70 may be prepared for delivery to an aperture 18 in any one of several ways. Slits 74 and 84 may be cut such that the tube bends into its intended configuration following deployment in vivo. Specifically, slits 74 and 84 may be cut to produce segments (as illustrated in FIGS. 5, 6) of a thickness that facilitates the bending and formation of petals 72 and 82 (as illustrated in FIGS. 7, 8) upon the application of forces $F_d$ and/or $F_p$ during deployment. The reference numerals 72 and 82 of FIG. 5 refer to the segments of material in a straight form. Whereas FIG. 6 shows these segments in the early stage of bending and twisting to form petals (shown fully deployed in FIG. 8.) As an alternative, or additionally, a tube formed of a shape memory material may be preformed into its intended configuration ex vivo so that it will recover its preformed shape once deployed in vivo. According to at least some embodiments, this performing technique produces more reliable deployment and bending of occluder 70 in vivo. An intermediate approach may also be used: the tube may be only slightly preformed ex vivo such that it is predisposed to bend into its intended shape in vivo upon application of forces $F_d$ and/or $F_p$. In other embodiments, the tube may be formed by arranging monofilaments in a tube-like configuration.

FIG. 2 shows a deployed occluder 70 in a human heart with a catch member engaged. The term "catch member" describes the portion/aspect of the device that secures the device in the deployed configuration; it may be a single piece or a group of connected or assembled pieces. A catch member 50 can be one or more parts of a catch system that engages with the occluder to hold the occluder in the deployed configuration and is described in more detail below. The configuration illustrated is a slightly simplified schematic view of the occluder 70 illustrated in FIGS. 5-8.

This particular type of occluder 70 and delivery sequences are described for purposes of illustration and explanation; of course, other types of occluders can be deployed using the deployment catch members described herein. The catch member 50, as illustrated generally in FIGS. 2, and 7-10, is disposed in a radially central location in the occluder 70 and is schematically illustrated as a separate piece from the occluder 70. In one embodiment, the catch member may be attached to the distal end of the tube that forms occluder 70 as illustrated in FIGS. 7-10. In another embodiment, a shelf that is fixed to an elongated piece of the catch member 50 can rest against the distal tip of the occluder. This is described further and illustrated with FIGS. 9 and 10 and accompanying text.

In general, references to "occluder 70" herein may be inclusive of catch member 50, depending on the context, for example, unless separately listed or otherwise stated. One end of the tube is able to move with respect to the catch member 50 so that the distal and proximal petals 72 and 82 can move from the delivery configuration to the deployed configuration. The inside surface of the tube is able to slide over the catch member 50 so that, when the proximal end of the catch member rests against a proximal end 86 of occluder 70, the occluder is secured in its deployed configuration. The catch member 50 is part of a catch system that also includes a portion for connection to the delivery/recovery system, such as, for example, a ball illustrated and described in more detail below.

Figure 3:
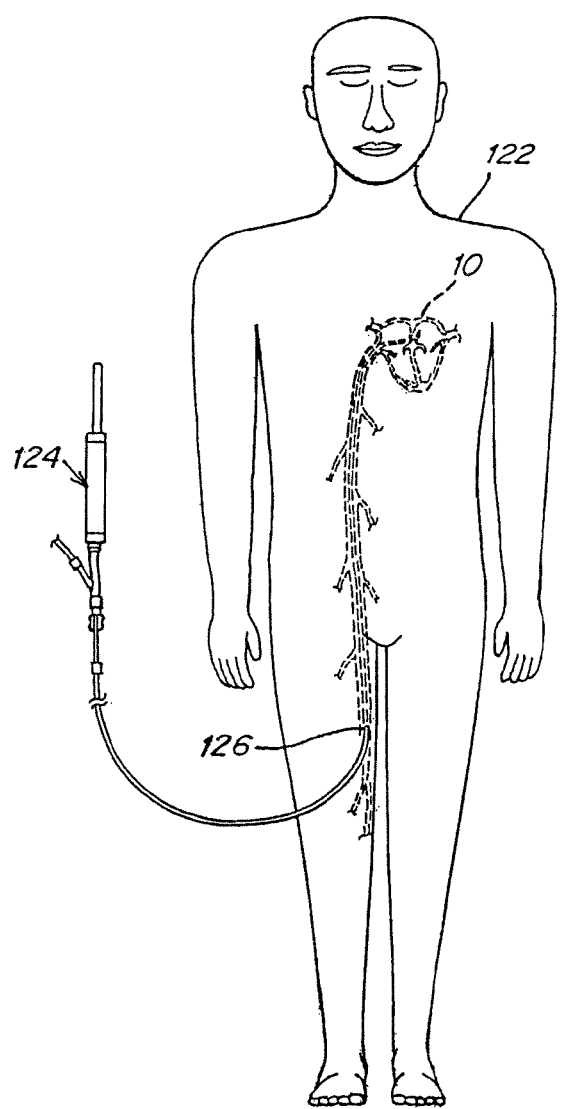
FIG. 3 illustrates introduction of an occluder in a human heart using a delivery system in accordance with an embodiment of the present invention.
Figure 4:
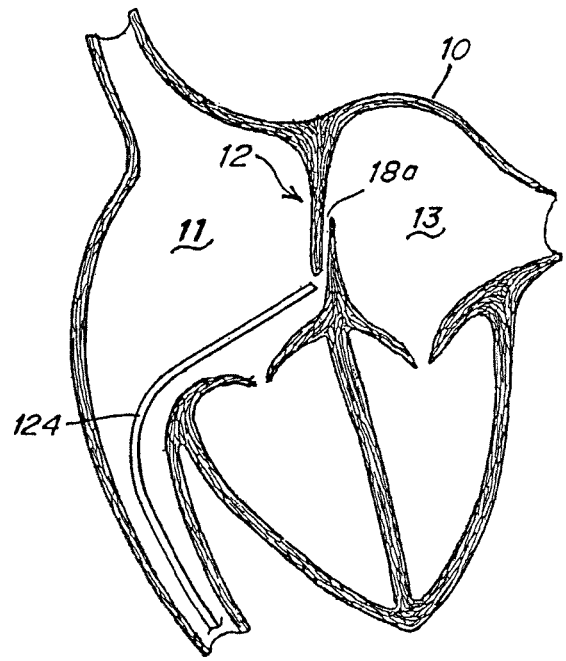
FIG. 4 illustrates a detail view of a delivery catheter in a heart with its tip approaching a patent foramen ovale between the left atrium and right atrium.

FIG. 3 illustrates the insertion of an occluder in a human subject 122 using a delivery assembly 124 in accordance with an aspect of the disclosure. A portion of delivery assembly 124, including an occluder and a delivery mechanism for the occluder, which can be externally manipulated by a clinician, is inserted into the subject through an incision point 126. The distal end of the delivery assembly is advanced toward and into the heart 10 until the distal end is in proximity to the defect to be closed, as seen in FIG. 4.

Figure 9:
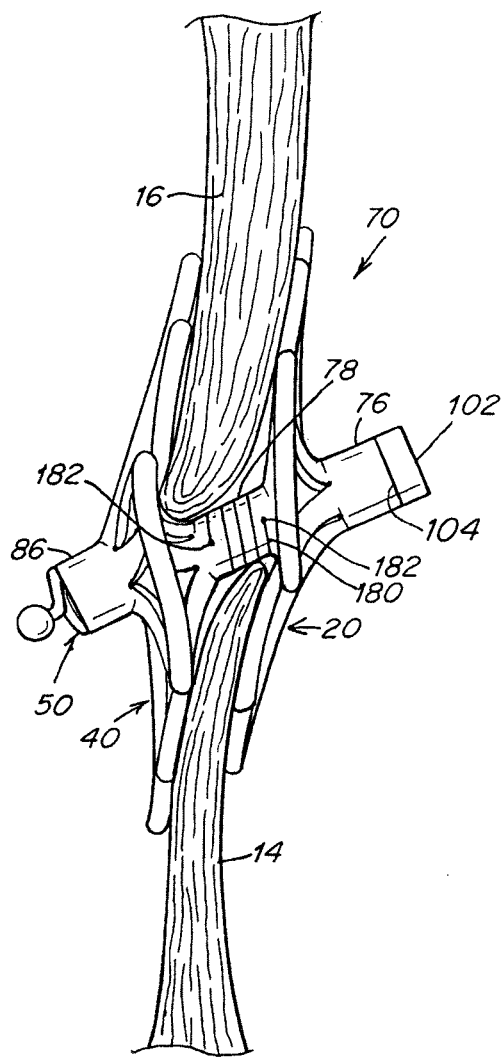
FIGS. 9-10 illustrate a detail view of an occluder according to an embodiment of the present invention.

An expandable center joint will now be described with reference to FIGS. 9-12E. FIG. 9 illustrates the catch member 50 that is adapted to be disposed in the center of the tubular portion of the occluder 70. The catch member 50 includes a distal end 102 that is disposed at the distal end of the occluder 70. In some embodiments, the distal end 102 of the catch member 50 is fixed to the occluder. In other embodiments, the catch member 50 is allowed to rotate with respect to the occluder. In one embodiment, the catch member 50 includes a distal shelf 104 that rests against the distal end 76 of the occluder 70, allowing the distal portion of the occluder to be moved along with the catch member 50 relative to the proximal portion when there is a $F_p$ or $F_d$ force applied as described in preceding paragraphs. Typically the catch member has an axial length of about 15 mm and a diameter of approximately 5 mm. Although a circular cylinder is illustrated, a variety of cross sectional shapes can by used effectively.

Figure 10:
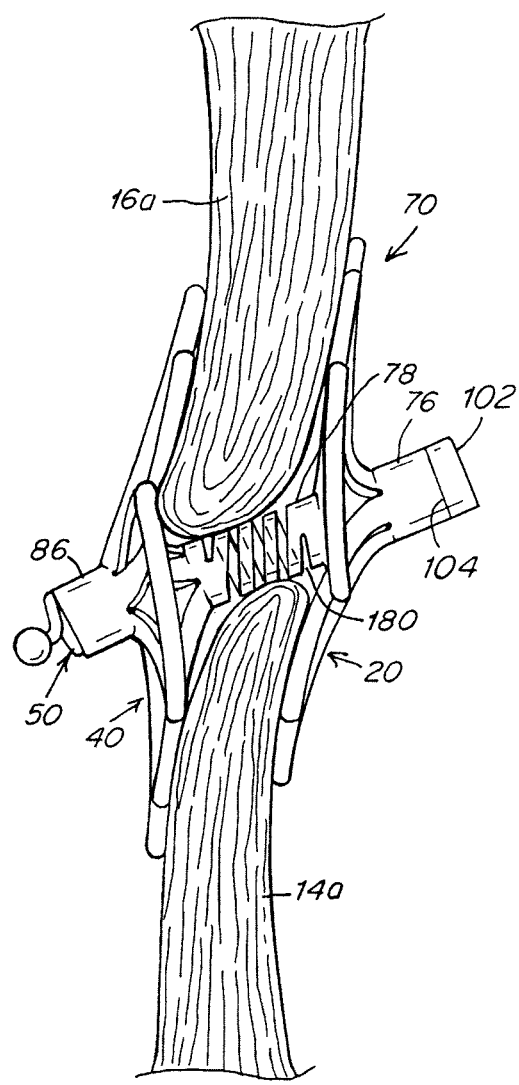

FIGS. 9-10 illustrate a detail view of an occluder constructed according to an embodiment of the present invention. As illustrated, the center joint 78 includes a spiral cut 180, which allows the joint to expand in an axial direction. The cut can be made using laser, heat, a razor, or other suitable techniques. As illustrated there are 4 turns in the spiral cut. More or fewer turns may be used to accomplish the axial elongation. Small holes 182 may be disposed at the end of the spiral cut to relieve stresses and reduce the possibility that the cut will extend beyond the desired length. Catch member 50 is designed to keep the device in the deployed configuration. Only a portion of the catch member 50 is illustrated.

FIG. 10 illustrates a thicker septum primum and secundum 14a, 16a, which causes the axial length of the device to expand when the device is deployed at the delivery site. Specifically, as illustrated, the spiral cut 180 allows the center joint 78 to elongate so that the device can securely fit within septa of different dimensions. This allows a single occluder to be able to be used in a number of different sized septa. Additionally, sometimes the PFO is angled, as illustrated in FIG. 1, and the length of the PFO would require a center joint that is longer than if the PFO tunnel were not angled. The expandable center joint can accommodate PFO tunnels that are at a variety of angles.

Figure 11:
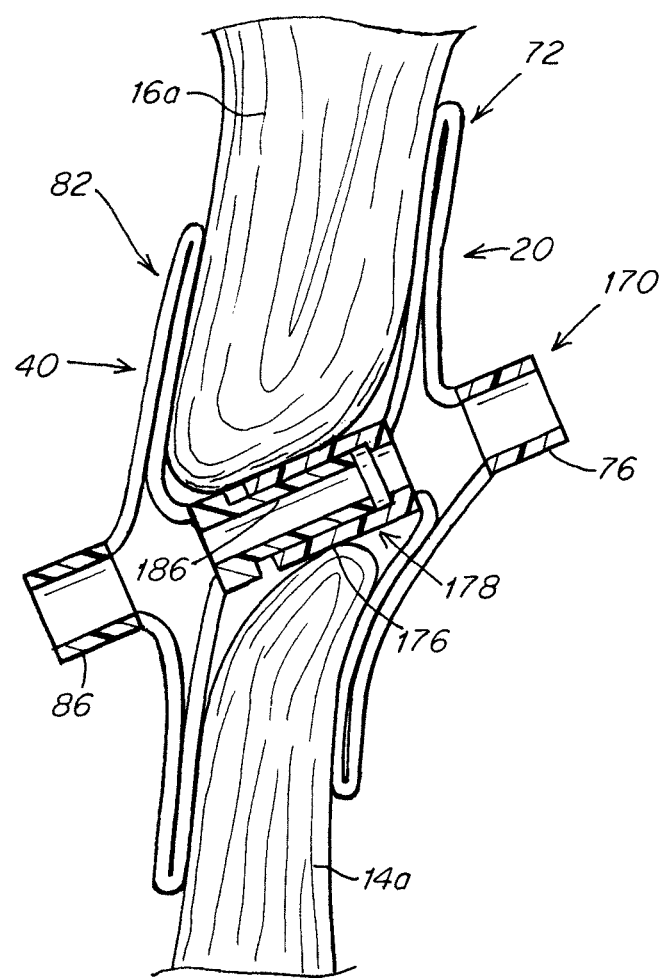
FIG. 11 is a cross-sectional view of an adjustable-length occluder device, in its deployed form, with the catch system omitted, according to an embodiment of the present invention.

FIG. 11 is a cross-sectional view of an adjustable-length occluder device 170 in its deployed form, according to another embodiment of the invention. The figure shows an occluder with an expandable, telescoping center joint 178 capable of adjusting to fit the dimensions of the particular tissue at the delivery site. For illustrative purposes, the catch member is not shown in FIG. 11. In preferred embodiments, a catch member, such as that illustrated in FIG. 12A-12E, is located in the center of the tubular portion of the occluder and axially aligned with the occluder. The catch member supplies the mechanism by which the occluder 170 is secured in the desired deployed configuration.

The telescoping center joint 178 of the occluder 170 allows the device to achieve an optimal fit for the tissue surrounding the defect. The telescoping center joint 178 is capable of an expanded configuration that provides a customized fit for a thick septum and a compressed configuration to fit a thin septum. The telescoping center joint feature is one of many possible alternatives to the adjustable length center joint 78 of FIG. 9-10, in which the spiral cut 180 allows for axial expansion of the occluder 70. Whereas the occluder 70 with an adjustable center joint 78 may be constructed from a single tube, the occluder 170 with a telescoping center joint 178 comprises two substantially tubular sections. The two substantially tubular portions include a proximal portion 40 and a distal portion 20. The distal section of proximal portion 40, forms a proximal portion 186 of the telescoping center joint 178. The proximal section of the distal portion 20 forms the distal portion 176 of the telescoping center joint 178. The junction of portions 186 and 176 thus forms the telescoping center joint 178. As shown in FIG. 11, the aforementioned portions of the occluder may be constructed so that the proximal portion 186 of the telescoping center joint 178 can be controllably inserted in to the distal portion 176 of the telescoping center joint 178. Alternately, the portions may be constructed so that the distal portion 176 can be controllably inserted into the proximal portion 186. When proximal portion 186 and distal portion 176 are joined to form telescoping center joint 178, they are not fixed but instead arranged so that they may controllably slide into or out of one another to a desired extent. Once occluder 170 is deployed, the extension of the telescoping center joint 178, in part, determines the total length of the deployed occluder.

According to a certain embodiment of the invention, the two substantially tubular portions of the occluder 170 are made in accordance with the techniques describe above with reference to the single occluder 70. The tubes that form proximal portion 40 and distal portion 20 can be injection molded, extruded, or constructed of a sheet of material and rolled into a tube. The sheet of material could be a single ply sheet or multiple ply. The slits that form the petals could be cut or stamped into a sheet prior to rolling the sheet into a tube to connect the ends to form an enclosed cross section. Various geometrical cross-sections are possible. Various attachment techniques could be used to join the ends of the sheet to form each tube. In yet other embodiments of the present invention, the tubes could be formed by arranging and joining monofilaments into a tube-like configuration.

As noted above, the occluder 170 shown in FIG. 11 is, in preferred embodiments, used with a catch member 150 depicted in FIG. 12A-12E. The catch member is disposed within the center of the tubular portion of the occluder 170 and used to secure the occluder in its deployed configuration at the delivery site. In the present embodiment, the extent to which the telescoping center joint 178 is expanded or compressed is controlled, in part, by the thickness of the septal tissue. The position of deployed proximal and distal petals 82 and 72, is controlled by the catch member 150 depicted in FIG. 12A-12E. By using catch member 150 according to the techniques describe below, the telescoping center joint 178 may be set to the desired length while the deployed proximal 82 and distal petals 72 have a fixed axial dimension, regardless of the length set for the center joint. That is, the distance between the distal part of the proximal end 86 and the proximal portion 186 is fixed when the proximal petals 82 are deployed. Likewise, the distance between the proximal part of distal end 76 and the distal portion 176 is fixed when the distal petals 72 are deployed. The specific mechanisms are described below.

FIG. 12A-12E illustrate a catch member 150, in various configurations, according to an embodiment of the present invention. The present catch member 150 has an adjustable axial length, for use with an occluder 170 having a telescoping center joint 178. The use of an adjustable-length catch member 150 in a septal closure device with a telescoping center joint permits the device to fit various septum thicknesses in a cardiac defect area. The present embodiment of the invention, when deployed, achieves a highly-customized fit for individual septal defects. That is, the present catch member 150 enables the occluder 170 to be fully deployed and have an axial length that is expanded or compressed to fit a range of thick or thin septums. FIGS. 12A-12E illustrate that the overall length of the occluder 170 is reduced during deployment. This length reduction can be as low as 50% or as great as 90% of the overall length of the occluder in the delivery configuration. For example, it is common for the length reduction to vary from 65% to 88%. Thus, while less than this amount of length reduction is shown in the figures, this is merely for convenience.

Figure 12A:
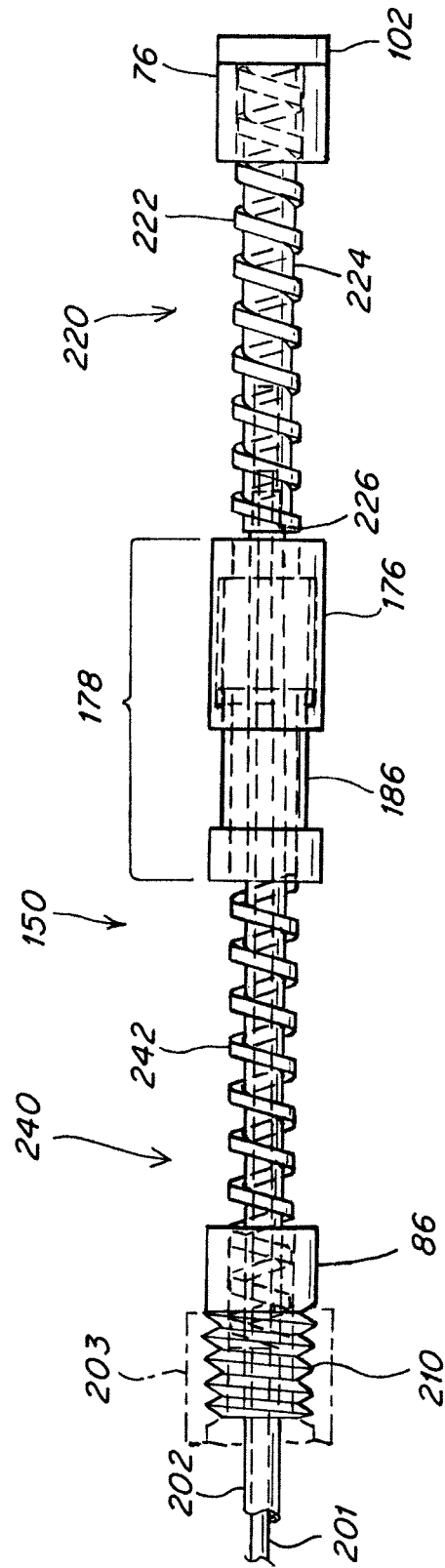

FIG. 12A illustrates the adjustable-length catch member 150 of the present embodiment with select portions of the occluder 170 and the delivery catheter system attachment mechanisms shown. The catch member has a proximal end and a distal end; the ends align with the proximal and distal ends of the occluder device, 86 and 76, respectively. The total axial distance between the proximal and distal ends of the catch member is herein referred to as the "catch length" and corresponds, substantially, to the total length of the occluder 170. FIG. 12A shows delivery catheter system attachments including the rotation transfer shaft 202 and the core wire 201 that runs through the center of the rotational transfer shaft 202. During deployment, the rotational transfer shaft 202 and the core wire 201 are used to controllably rotate and position the distal end and the proximal end of the catch member relative to one another and relative to the distal end 76 and proximal end 86 of the adjustable-length occluder. The mechanism of deployment is described more fully, below.

Catch member 150 comprises a proximal section 240 and a distal section 220. Proximal section 240 comprises a series of spiral threads 242 that align to form an approximately tubular structure. In certain embodiments, the material used for proximal section 240 of the catch member is the same as the occluder material; while in other embodiments, it could be different from the occluder material. Distal section 220 comprises a substantially tubular section 224 with spiral threads 222 disposed on the outer surface. In certain embodiments, the material used for distal section 220 of the catch member is the same as the occluder material; while in other embodiments, it could be different from the occluder material. The axial length of the catch member 150—the catch length—is adjusted during deployment by controllably threading distal section 220 into the center of proximal section 240 so that spiral thread 242 and 222 are aligned and engaged. Thus, the catch length of the catch member 150 is determined by the extent to which the distal 220 and proximal 240 sections are engaged. Although the embodiments described herein have interlocking spiral threads, the proximal sections can be an outer threaded tube member and the distal section can be an inner threaded tube member (or vice versa) to accomplish similar results.

In the manner described above, the total catch length of the catch member 150 can be adjusted. During deployment, the position of the occluder device 170 is adjusted in relation to the catch member 150. In certain embodiments, proximal section 240 of the catch member has a proximal end that is fixed with respect to the proximal end of the occluder device 86 and remains attached throughout delivery and deployment of the occluder. The proximal end of the occluder device 86 may have a securement mechanism that secures the occluder to a delivery system. Such a delivery system can attach to the proximal end of the occluder 86 by, for example, spiral threads 210, circumferential loops or other suitable means.

According to certain embodiments of the invention, distal section 220 has a distal end 102 that rotates freely with respect to the distal end 76 of the occluder 170. During insertion of the device, the distal end 102 of the distal section 220 is attached to core wire 201 which controls the axial positioning of the distal end of the catch member 150. The proximal end of the distal section 220 further includes a small thread, Niti hook, or other component 226. Any such component 226 prevents the distal section 220 of the catch member 240 from disengaging from the core wire 201 until desired. Distal section 220 also has a proximal end that, upon deployment of the occluder 170, connects to the distal end of the proximal section 240 of the catch member 150. Specifically, spiral threads 222 engage with spiral threads 242 to position distal section 220 in relation to the proximal section 240. Alternate mechanisms for engaging proximal section 240 and distal section 220 of the catch member 150 are also possible and may also be effectively employed to secure the occluder 170 in its deployed configuration with the desired catch length and remain within the scope of the invention.

By connecting the proximal and distal sections of the catch member in this manner, the total catch length, as measured between the proximal end of the proximal section 240 and the distal end of the distal section 220, can be controllably varied. Because the proximal end of the catch member engages with the proximal end of the occluder 86 and the distal end of the catch member engages with the distal end of the occluder 76, the total catch length controls, in part, the length and deployment of the occluder 170.

Deployment of the occluders 70 and/or 170 with the catch member 150 enables the adjustment of the above-mentioned components to achieve a customized fit for an individual defect. The deployment process is now described in detail.

The adjustable length septal occluder and the catch member are first inserted and positioned at the delivery site. The techniques, mechanism (e.g., catheter systems) and steps for insertion and positioning of the occluder device in the septal defect are known in the art and thoroughly described in the incorporated references. In particular, U.S. patent application Ser. No. 11/235,661, entitled Occluder Device Double Securement System for Delivery/Recovery of Such Occluder Device, filed Sep. 26, 2005, incorporated by reference herein in their entirety, details various delivery methods. It will be appreciated by one skilled in the art that the preferred delivery mechanisms and techniques for inserting the present occluder device at the delivery site will be determined, in part, by the particular application and individual patient.

FIG. 13A illustrates a cross-sectional view of the catch member 150. For clarity, the proximal section 240 and distal section 220 are shown as set apart from center joint 178. As mentioned above, rotational transfer shaft 202 (not shown) engages distal section 220 to controllably rotate and position the distal end and the proximal end of the catch member relative to one another and relative to the distal end 76 and proximal end 86 of the adjustable-length occluder. Distal section 220 has a slot 205 for receiving a key on the end of rotational transfer shaft 202, described below.

Figure 13C:
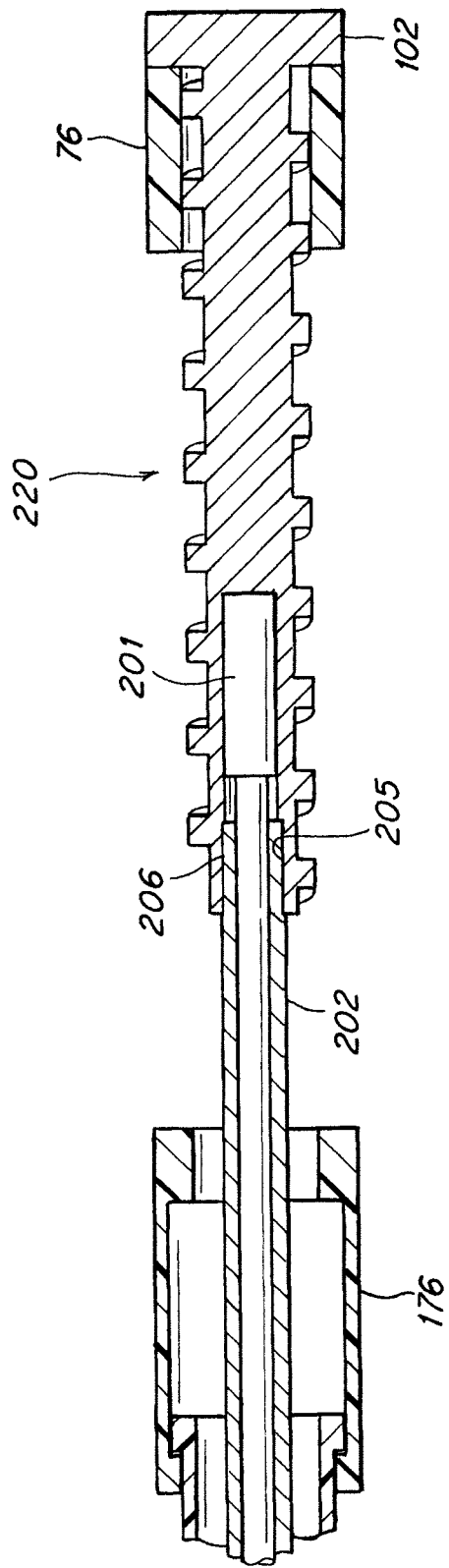

FIG. 13B shows the cross-sectional view of the catch member 150 of FIG. 13A including rotational transfer shaft 202. Rotational transfer shaft 202 has a keyed end 206 that engages the slot 205 of distal section 220. FIG. 13C provides a magnified view of distal section 220, illustrating the keyed end 206 of the rotational transfer shaft engaged in the slot 205 of the distal section 220. By mating the rotational transfer shaft 202 to the distal section 220, the cooperation of keyed end 206 and slot 205 allow the rotational transfer shaft 202 to apply torque to the distal section 220, thereby causing the threads of the distal section 220 to engage the threads of the proximal section 240. The complementary shape of keyed end 206 and slot 205 can be any shape suitable for transferring rotational force, for example, a square, triangular, or star shape. FIGS. 13B and 13C also show the distal end of the core wire 201.

During deployment, the rotational transfer shaft 202 and the core wire 201 are used to controllably rotate and position the distal section 220 and the proximal section 240 of the catch member relative to one another and relative to the distal end 76 and proximal end 86 of the adjustable-length occluder 170. In preferred embodiments, rotational transfer shaft 202 is a hollow structure and the core wire 201 is disposed along the hollow center. Both are axially disposed through the hollow center of the catch member 150 which, in turn is axially disposed along the center of the occluder 170 (note that only a portion of distal section 220 may be hollow). The core wire 201 is connected to the catch member's distal section 220 allowing for its controlled rotation, pushing, or pulling relative to the occluder 170. The rotational transfer shaft 202, connected to the distal section 220 of the catch member, is used to control and position, rotationally and axially, the distal section 220 of the catch member 150 with respect to the proximal section 240 of the catch member 150. As noted above, the proximal section 240 of the catch member is fixed with respect to the proximal section of the occluder 170 at proximal end 86. Thus, the rotational transfer shaft 202 can also effectively control the position of proximal section 240. This is so because once the distal section 220 has been fully deployed, further rotation of the rotational transfer shaft 202 will cause the proximal end 86 to move toward the proximal portion 186 of the telescoping center joint 178, thereby deploying the proximal section 240. An occluder delivery catheter 203 is attached to the proximal end 86 (as shown in FIG. 12A.) Thus, the occluder delivery catheter 203 holds the proximal end 86 and the proximal section 240 affixed thereto in a fixed position while rotational transfer shaft 202 rotates relative to the occluder delivery catheter 203. The proximal and distal portions of the telescoping center joint, 186 and 176, respectively, move freely with respect to each other, in response to the position of the catch member, the dimensions of the septal tissue at the insertion site and other device characteristics.

Referring again to FIG. 12A, the catch member 150 and only select portions of the occluder 170 are shown. Omitted from the illustration are the proximal and distal petals (82 and 72, respectively) as shown in their deployed form in FIG. 8. Proximal petals 82 are formed from the tube that comprises the proximal portion 40 of the occluder. Proximal petals 82 are circumferentially disposed and radially aligned around the proximal section 240 of the catch member that is disposed within the tube that comprises the proximal portion 40 of the occluder. The axial distance between the proximal end of the occluder 86 and the proximal end of the proximal portion 186 of the telescoping center joint determines the extension of proximal petals 82 during deployment. Similarly, distal petals 72 are formed from the tube that comprises the distal portion 20 of the occluder. Correspondingly, distal petals 72 are circumferentially disposed and radially aligned around the distal section 220 of the catch member that is disposed within the tube that comprises the distal portion 20 of the occluder. The axial distance between the distal end of the occluder 76 and the distal end of the distal portion 176 of the telescoping center joint determines the extension of distal petals 72 during deployment. The above-mentioned proximal and distal axial distances necessary for full deployment of the petals are selected by the specific design characteristics of the occluder 170 and achieved by using the catch member.

During delivery or implantation, when the occluder 170 is in its low-profile form and the petals are retracted, the axial distance between the proximal end 86 of the occluder and the proximal end of the proximal portion 186 of the telescoping center joint 178 is maximized. Similarly, the axial distance between the distal end 76 of the occluder and the distal end of the distal portion 176 of the telescoping center joint 178 is maximized. The low-profile form utilized during implantation of the occluder 170, when the petals are retracted, is shown in FIG. 5. Correspondingly, FIG. 12B shows the position of the catch member 150, as used with occluder 170 in the collapsed or low-profile, elongated form, during implantation. At the delivery or implantation stage, the proximal section 240 of the catch member and the distal section 220 of the catch member are not engaged with one another. Instead, the proximal section 240, fixed to the proximal end 86 of the occluder and the distal section 220, connected to the distal end 76 of the occluder are separated, axially, by a gap. As shown in FIG. 12B, neither the proximal section 240 nor the distal section 220 extend into the telescoping center joint 178 of the occluder 170. FIG. 12B shows the occluder 170, during implantation, with the telescoping center joint 178 in its most extended configuration wherein the overlap between the proximal portion 186 and distal portion 176 of the joint is comparatively minimized. In certain embodiments of the present invention, it may be preferable, instead, to deliver the occluder 170 with its telescoping center joint 178 in a compressed configuration wherein the proximal portion 186 and distal portion 176 of the joint overlap to a comparatively greater extent. Such a configuration allows the extent of expansion of the telescoping center joint 178 to be determined, in part, by the thickness of the septal tissue as the distal and proximal petals compress the septal tissue during deployment.

FIG. 12C illustrates the catch member in a first stage of deployment, according to certain embodiments of the invention. In the first stage, the distal petals 72 are positioned in their extended form. In their deployed configuration, distal petals 72 engage with the distal side of the septal tissue at the delivery site. The corresponding position of occluder petals can be seen in FIG. 7. To create this configuration, the axial distance between the distal portion 176 of the telescoping center joint 178 and the distal end 76 of the occluder is reduced. As noted above, the distal end 102 of the distal section 220 of the catch member can rotate freely with respect to the distal end 76 but is constructed and arranged to be capable of applying force $F_d$, shown in FIG. 6, to the occluder 170. To reduce the axial length of the distal portion 20 of the occluder 170 in this manner, core wire 201, affixed to distal end 102, is manipulated and retracted towards the proximal end of the insertion site as the rotational transfer shaft 202 rotates the distal section 220 relative to the proximal section 240. Correspondingly, the distal section of the catch member 220 is retracted into the distal portion 176 of the telescoping center joint as shown in region 220A.

During this first stage of deployment—distal compression—the proximal portion 40 of the occluder 170 is substantially maintained in its delivery configuration. The proximal section of the catch member 240 remains substantially fixed with respect to the proximal end 86 of the occluder. Both the proximal section 240 of the catch member 150 and the occluder 170 are maintained in a substantially axially-fixed position with respect to the delivery system (or delivery site) by use of the occluder delivery catheter 203. The distal section 220 of the catch member 150 (and the occluder 170) are maintained in a substantially rotationally-fixed position by the use of the rotational transfer shaft 202. As noted above, various delivery systems are known in the art and described in detail in the incorporated references.

At this point during delivery, distal threads 222 are positioned to engage with proximal threads 242. The initial engagement of the threads occurs within telescoping center joint 178 of the occluder 170. Thus, during the first stage of deployment, the proximal portion 40 of the occluder remains in the elongated delivery configuration by virtue of remaining enclosed in the occluder delivery catheter 203, and the distal portion 20 of the occluder is secured in the deployed configuration. In the present embodiment, the distal petals 72 and the proximal petals 82 of the occluder are locked after both of them are deployed, as described in detail below. Variations on the present deployment sequence may be preferable in alternate applications and may be envisioned by those sufficiently skilled in the art.

By using the present adjustable axial length catch member in combination with an occluder 170 having a telescoping center joint, a number of adjustments may be made to the shape, size and position of the device during implantation and deployment. In preferred embodiments, the adjustability provides a customized fit and highly effective occlusion of differently dimensioned septal defects. FIGS. 12D and 12E show how the occlusion device may be arranged to provide an individualized and customized fit for septal defects of different dimensions.

FIGS. 12D and 12E illustrate portions of the occluder 170 and catch member 150 at the second stage of deployment in which the proximal petals 82 are positioned in the deployed configuration and are used to apply compressive force to the proximal side of the tissue at the implant site. The corresponding position of the petals can be seen in FIG. 8. In this stage, the proximal portion 40 of the occluder 170 is transformed from the compressed, delivery position to the deployed configuration by reducing the axial length of the proximal section 240 of the catch member 150 between the proximal portion 186 of the center joint 178 and the proximal end 86 of the occluder 170. To achieve this configuration, the rotational transfer shaft 202 is used to controllably rotate the distal section 220 of the catch member with respect to the proximal section 240 of the catch member. As the distal section 220 is controllably rotated, distal threads 222 engage with proximal threads 242 thereby decreasing the total axial length of the catch member 150. The proximal section 240 of the catch member is drawn into the proximal portion 186 of the telescoping center joint 178, as shown in region 240A. At the same time, the extension of the adjustable length center joint 178 of the occluder adjusts to fit the tissue of the defect in which it has been implanted. This fit is achieved because the proximal and distal portions of the telescoping center joint shown in FIG. 11 and FIG. 12 (186 and 176, respectively) slide freely with respect to each other and in response to the position of the catch member elements (and septal tissues). The fit is achieved when the proximal and distal petals (82 and 72, respectively) substantially contact the proximal and distal surfaces of the septal tissue.

While proximal and distal portions of the telescoping center joint, 186 and 176, slide freely with respect to each other, in preferred embodiments, a stop mechanism 280 is used to prevent the distal and proximal portions of the telescoping center joint from separating through over-expansion. In certain instances, a latch formed by conformal ridges on the distal and proximal portions, 176 and 186, may be preferred, though any number of stop mechanisms 280 may be envisioned by a person skilled in the art.

The adjustability of the device is shown in the examples of FIGS. 12D and 12E. FIG. 12D shows portions of the occluder device 170 and catch member 150 in the deployed position for occluding a tissue defect in a thick septum. During the second stage of deployment, as described above, the total catch length is adjusted so that distance 340 between the proximal end 86 of the proximal portion 40 of the occluder and the proximal end of the proximal portion 186 of the telescoping center joint 178 is selected to fully deploy the proximal petals 82. The distance 320 between the distal end 76 of the distal portion 20 of the occluder and the distal end of the distal portion 176 of the telescoping center joint is selected to fully deploy the distal petals 72. By controllably threading distal section 220 into proximal section 240, the petals (72, 82) fully deploy and apply compressive force to the sides of the septal tissue. The distal and proximal portions of the telescoping center joint (176, 186) freely slide to accommodate the thickness of the particular septum. Thus, for the thick septum configuration shown in FIG. 12D, the telescoping center joint 178 is relatively extended, with the distal and proximal portions, 176 and 186, overlapping to a lesser extent.

Conversely, FIG. 12E shows portions of the occluder device 170 and catch mechanism 150 in the deployed position for occluding a tissue defect in a thin septum. Distances 340 and 320 are set such that the proximal petals 82 and distal petals 72 are fully deployed. Distal section 220 of the catch member is controllably threaded into the proximal section 240 of the catch member. In the case of the thin septal tissue, more threads (222 and 242) are engaged, than in the case of the thick septal tissue (e.g., FIG. 12D). Correspondingly, compressive force is applied to the septal tissue when the telescoping center joint 178 is relatively un-extended with distal and proximal portions, 176 and 186, overlapping to a greater extent. Thus, a desired length of telescoping center joint 178 is achieved, in part, by the extent to which the proximal petals 82 and distal petals 72 are deployed, as this determines, in part, the amount of compressive force applied to the septal tissue by the proximal petals 82 and distal petals 72.

Once the occluder has been properly deployed at the insertion site and the catch mechanism has been adjusted to provide an optimal fit of the septal defect, the occluder may be secured by any number of locking mechanisms. Various locking mechanism to prevent the distal and proximal sections of the catch member (220 and 240) and respective threads (222, 242) from moving after deployment, and thereby altering the catch length, are envisioned and may be selected by one sufficiently skilled in the art.

There is a balance of forces that desirably secures the occluder in place without compressing the septum in a manner that would produce an adverse tissue reaction. Accordingly, the axial force required for the expansion of the center joint in an axial direction should be about the same as the compressive force applied by the catch member when in the deployed configuration. If the force applied by the catch member is too great, the tissue between the occluder pedals could have an adverse reaction.

In these adjustable length center joints, the optimum fit for each patient is achieved by either choosing a proper length catch member or by incorporating the adjustable length catch member disclosed earlier.

In certain embodiments of the present invention, each of the proximal portion 40 and distal portion 20 of the occluder device are made of a polymer and formed from a single tube, such that the tube is a single monolithic material. While the device 170 is thus shown as being substantially formed from proximal and distal tubular bodies, the catch member as described in the embodiments above could be used with other types of devices, including those formed from many pieces, and including devices formed from other materials, including metals, polymers, stainless steel or nitinol.

Figure 14A:
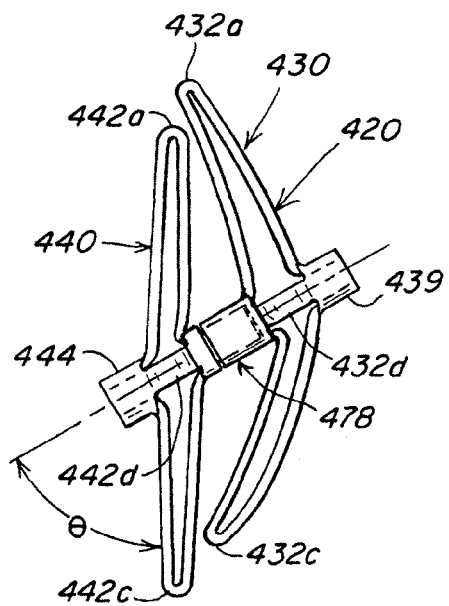
FIGS. 14A-C illustrate an occluder with linearly elongating loops for use with the variable-length catch member, according an embodiment of the present invention.
Figure 14B:
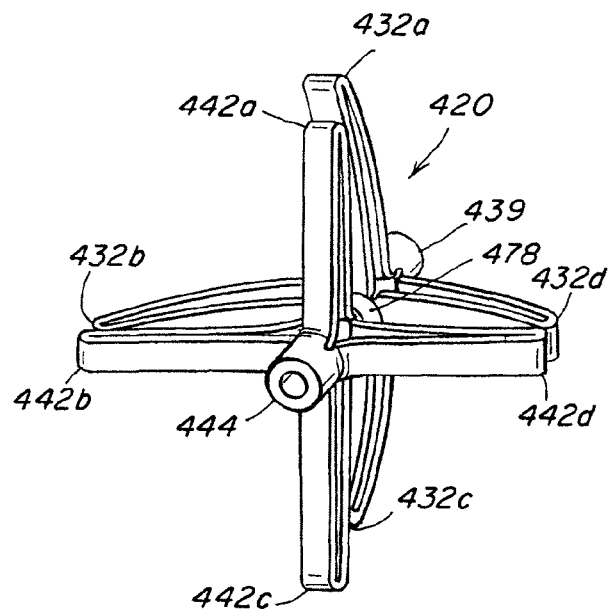
Figure 14C:
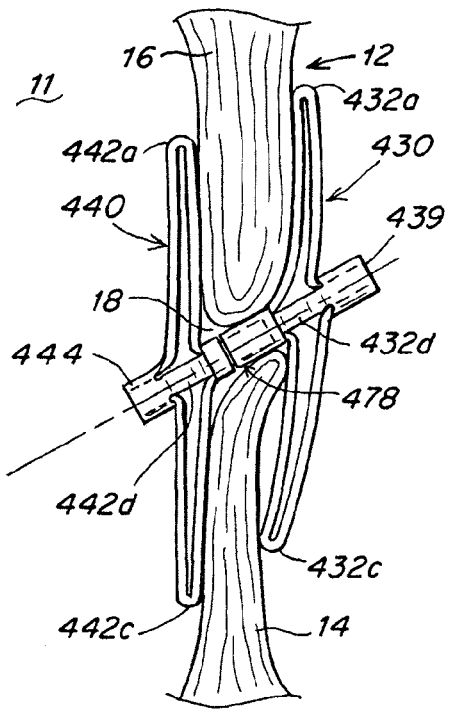

In addition, the occluders have been described above as having loops, hoops, or petals that expand radially when the axial length of the proximal and distal portions of the occluder are reduced. However, other embodiments include linearly elongating loops, such as those described in U.S. patent application Ser. No. 11/728,694, entitled Patent Foramen Ovale (PFO) Closure Device with Linearly Elongating Petals, filed Mar. 27, 2007, incorporated above. FIGS. 14A-14C illustrate an example of such an occluder 420, having proximal portion 440 and a distal portion 430. The proximal portion 440 has loops 442a-442d that extend radially from the central axis of the occluder. Likewise, distal portion 430 has loops 432a-432d that extend radially from the central axis of the occluder. Similar to the occluders described above, occluder 420 has a proximal end 444 and a distal end 439. FIGS. 14A-14C show the occluder 420 in the fully deployed configuration.

Figure 15A:
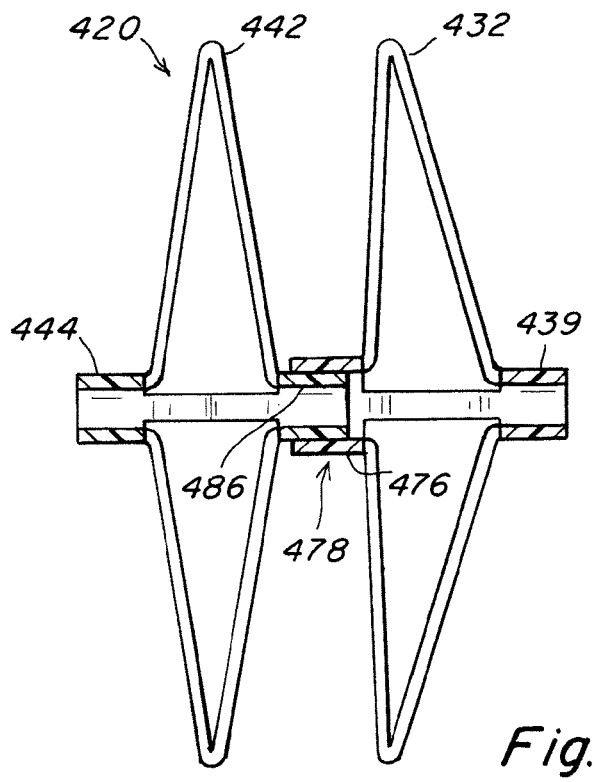
FIGS. 15A-B illustrate a cross-sectional view of the occluder of FIGS. 14A-C.
Figure 15B:
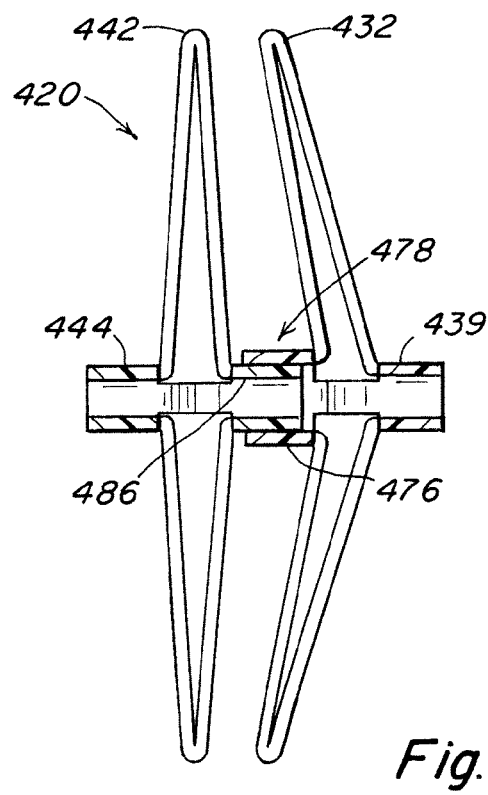

FIGS. 15A and 15B illustrate a cross-sectional view of the occluder 420 having a telescoping center joint 478, as described above. (In other embodiments, a spiral cut center joint is provided.) Thus, the variable-length catch member 150, described above, can be used with occluder 420. As in the embodiments described above, the proximal section and distal sections of the catch member 150 can slide rotationally relative to each other to reduce the axial distance between the distal end 439 and proximal end 444 of the occluder. In effect, the relative movement of the proximal and distal sections of the catch member 150 controls the tissue clamping force imposed by the distal and proximal portions of the occluder to the septum. In one embodiment, the adjustable catch length, in combination with the free sliding telescoping center joint of the occluder, enable an operator to control and maintain the tissue clamping force as desired.

The term "bioabsorbable," as used in the description above, is also understood to mean "bioresorbable."

While the description above refers to strings, filaments, sutures and wires, and while the term "wire" might convey a more rigid piece than a string, a suture or a filament, all these terms are essentially interchangeable, and further include embodiments in which the wire, string, suture or filament is a hollow tube or conduit to allow another wire, as needed, to pass through its longitudinal axis. Each wire, string, suture and filament can be composed of one or more wires, strings, sutures and filaments.

In cases in which the device is made of a polymer, it can be desirable to add an additive or coating to the material to make it radiopaque to make it more visible in a wider variety of imaging techniques.

It will be appreciated that while a particular sequence of steps has been shown and described for purposes of explanation, the sequence may be varied in certain respects, or the steps may be combined, while still obtaining the desired deployment or in some cases to effect deployment in a particular way. For example, the delivery sheath may be advanced or retracted at varying times and in varying degrees, the proximal and distal portions of the occluder may be deployed into the petal configuration in a different sequence, etc. In addition, the steps could be automated.

What is claimed is:

1. A collapsible medical device for occluding an aperture in a body including a distal side and a proximal side, the medical device having a first configuration with a reduced profile and a second configuration with an expanded profile, the medical device being adapted to be delivered through a delivery system into a desired delivery location, the collapsible medical device comprising:
   a distal end and a distal portion for contacting the distal side of tissue through which the aperture is present;
   a proximal end and a proximal portion for contacting the proximal side of tissue through which the aperture is present;
   a center joint adapted to extend through the aperture at an opening and being hollow in the center, the center joint engaging the distal portion and the proximal portion, and the center joint having a variable length; and
   a catch system for holding the collapsible medical device in the second configuration, the catch system having an adjustable catch length, the catch system including a distal threaded catch portion engaging the distal end and a proximal threaded catch portion engaging the proximal end, wherein the distal threaded catch portion comprises a proximal end that connects to a distal end of the proximal threaded catch portion, the threaded portions rotating relative to one another and cooperating through the hollow center joint to adjust the catch length, and wherein the center joint and catch system are indirectly coupled and operable to generate a balanced axially compressive force in the second configuration.

2. The medical device of claim 1, wherein the center joint is a telescoping center joint.

3. The medical device of claim 1, further comprising a locking mechanism to prevent rotation of the threaded portions relative to one another after a desired center joint length has been achieved.

4. The medical device of claim 1, wherein the expanded profile is achieved by reducing the distance between the distal and proximal ends.

5. The medical device of claim 4, wherein the length of the center joint is variable when the medical device is in the first configuration and when in the second configuration.

6. The medical device of claim 4, wherein an axial force required to expand the length of the center joint is substantially equal to the force exerted by the catch system to achieve the expanded profile.

7. The medical device of claim 1, wherein the catch system is made of polymeric material including at least one of bioabsorbable polymer and shape-memory polymer.

8. The medical device of claim 1, wherein the catch system is made of a biocompatible metal material.

9. The medical device of claim 1, further comprising a securement system for attaching the catch system to a delivery wire and attaching the medical device to a delivery catheter.

10. The medical device of claim 1, wherein the medical device is made from at least one material selected from a biocompatible metal, a bioabsorbable polymer and a shape-memory polymer.

11. The medical device of claim 1, wherein the medical device in the first configuration is substantially cylindrical in shape and in the second configuration includes a distal set and a proximal set of petals, circumferentially arranged and radially oriented, adapted to provide clamping force on opposite sides of the aperture.

12. The medical device of claim 1, wherein the medical device is constructed from a substantially cylindrical portion of material with a proximal and a distal series of axial slits, each series of axial slits arranged circumferentially.

13. A collapsible medical device for occluding an aperture in a body, the medical device having a first configuration as a reduced profile and a second configuration as an expanded profile, the medical device being adapted to be delivered through a delivery system into a desired delivery location, the collapsible medical device comprising:

a proximal side and a distal side for covering opposite sides of the aperture and an adjustable-length hollow center joint defining a lumen, the center joint being disposed between the proximal side and the distal side capable of extending and retracting in an axial direction; and a catch system engaging the proximal side and the distal side for holding the collapsible medical device in the second configuration, the catch system having an adjustable catch length, the catch system including cooperating threaded members adapted to be disposed in the lumen of the center joint such that the medical device can move from the first configuration to the second configuration, the cooperating threaded members being rotatable relative to one another to adjust the catch length, and wherein the center joint and catch system are indirectly coupled and operable to generate a balanced axially compressive force in the second configuration.

14. The medical device of claim 13, wherein the adjustable-length center joint includes at least one spirally oriented cut, constructed and arranged to allow flexible deformation of the adjustable-length center joint.

15. The medical device of claim 13, wherein the adjustable-length center joint includes a first portion and a second portion, the first portion having a first cylinder with first circumferential features on an inner surface and the second portion having a second cylinder with second circumferential features on an outer surface; the second portion capable of being controllably inserted in the first portion such that the first features of the proximal portion and the second features of the distal portion are in contact and wherein contact between the first features of the proximal portion and second features of the distal portion secures said adjustable-length center joint at a selected length.

16. The medical device of claim 15, wherein the inner surface of the first portion and the outer surface of the second portion are further contoured to provide substantial friction when the inner surface of the first portion is brought into contact with the outer surface of the second portion.

17. The medical device of claim 13, wherein the device is adapted to close a septal defect including a patent foramen ovale (PFO).

18. The medical device of claim 13, wherein the proximal and distal sides include a plurality of loops in the second configuration, and the loops are adapted to exert compressive force on opposite sides of the aperture.

* * * * *